US006616668B2

(12) United States Patent
Altarac et al.

(10) Patent No.: US 6,616,668 B2
(45) Date of Patent: Sep. 9, 2003

(54) ADJUSTABLE TRANSVERSE CONNECTOR FOR USE WITH A SPINAL IMPLANT SYSTEM

(75) Inventors: Moti Altarac, Aliso Viejo, CA (US); Philip A. Meilinger, Ladera Ranch, CA (US)

(73) Assignee: Cross Medical Products, Inc., Irvine, CA (US)

( * ) Notice: Subject to any disclaimer, the term of this patent is extended or adjusted under 35 U.S.C. 154(b) by 0 days.

(21) Appl. No.: 09/855,307

(22) Filed: May 15, 2001

(65) Prior Publication Data
US 2002/0032442 A1 Mar. 14, 2002

Related U.S. Application Data
(60) Provisional application No. 60/210,806, filed on Jun. 9, 2000.

(51) Int. Cl.[7] ................................................ A61B 17/56
(52) U.S. Cl. .................... 606/61; 606/63; 623/17.11; 623/17.14
(58) Field of Search ................. 606/61, 69, 70, 606/71, 63; 623/17.11, 17.14, 17.15

(56) References Cited

U.S. PATENT DOCUMENTS

| 5,275,600 A | * | 1/1994 | Allard et al. ................. 606/61 |
| 5,688,272 A | | 11/1997 | Montague et al. |
| 5,752,955 A | | 5/1998 | Errico |
| 5,947,966 A | | 9/1999 | Drewry et al. |
| 6,110,173 A | * | 8/2000 | Thomas, Jr. ................. 606/61 |
| 6,113,600 A | * | 9/2000 | Drummond et al. .......... 606/61 |
| 6,136,003 A | | 10/2000 | Hoeck et al. |

FOREIGN PATENT DOCUMENTS

| EP | 0 594 236 | 4/1993 |
| WO | WO 00/15126 | 3/2000 |
| WO | WO 00/57801 | 10/2000 |
| WO | WO01/12087 | 2/2001 |

* cited by examiner

Primary Examiner—Gregory L. Huson
Assistant Examiner—Amanda Flynn
(74) Attorney, Agent, or Firm—Laura F. Shunk; Hudak, Shunk & Farine Co. LPA

(57) ABSTRACT

The present invention relates to a transverse connector having an assembly, which joins two spinal rods to form a spinal implant construct. The transverse connector has two members each having terminal clamping members such as opposing rod recesses each having a biasing setscrew, which locks the rod into position in the recess. The first of the two members has a bore, which receives the cylindrical extension of the other part so that it can move inward and outward and rotate in the bore. Further, the connector has a limiting mechanism, which comprises a vertical keyway which receives and captures the flanged end of the extension in a slot having opposed undercut areas so that the flanged end can be inserted into the keyway and slid downward toward the bore. The extension further has a second flanged area in order to avoid over-insertion of the second member into the first member.

18 Claims, 3 Drawing Sheets

ADJUSTABLE TRANSVERSE CONNECTOR FOR USE WITH A SPINAL IMPLANT SYSTEM

This patent application is based upon U.S. Provisional Application Ser. No. 60/210,806 filed Jun. 9, 2000.

FIELD OF THE INVENTION

The invention relates generally to an implant system for the stabilization of the spine, and more particularly to a transverse connector, which is conveniently adjustable for connection of two lateral stabilizer members, i.e. spinal rods, which span the length of multiple vertebrae.

BACKGROUND OF THE INVENTION

The field of orthopedics has grown in its development of spinal stabilization systems, which can be surgically implanted in order to remedy a number of medical indications, such as for example, spinal curvatures and fixation for stability in fusion procedures. Implant design must include considerations of the obfuscation within the biological environment, and the stress of in-situ surgical assembly. Spinal surgeons work with a very limited space with great concern as to minimizing the amount of time that the procedure takes, and avoiding undue disruption to the surrounding tissues. While the components of the system are small, it is important that they are as easy to assemble as possible and that they are not cumbersome.

Typically, spinal stabilization systems comprise an elongated stabilizer which can be a cable or plate member, but most often comprises a rod. The rod is held in position, usually on the posterior side of at least two vertebrae alongside the spinous process, by anchoring members which have a component that secures or clamps the rod into a fixed position longitudinally, and a component that secures the anchor in place relative to the vertebral body, i.e. a hook or screw. Of course, the anchor can be an integral unit with the screw or hook securing member. Thus with respect to the present invention, a first assembly includes a stabilizer rod or plate, and multiple anchoring members. Typically a spinal construct will include two such assemblies, one on each lateral side of the spinous processes. In order to impart further stability to the construct, it typically also includes laterally extending members which connect the two stabilizers. These connecting members are often termed "transverse connectors".

The present invention relates to a transverse connector design, which has an adjustable length to its longitudinal linking portion. This linking area constitutes a linking assembly which joins the clamping or locking members which clamp or lock the transverse connector to the stabilizers. The present invention could include various clamping or locking means such as a rod or plate receiving recess and biasing member, which is preferably a setscrew, or vise arms or other means which form an interlocking engagement between the clamping or locking member, and rod or plate stabilizer.

The linking assembly includes two members. One is a first receiving member which has a recess to receive an extension of the second member. This structure forms a telescoping relationship between the first and the second parts of the transverse connector. A setscrew or the like can be used to lock the parts into a desired relative position when it has been achieved. The first or receiving member also has a sliding keyway which enables the parts to be disengaged or engaged but which further provides a means for limiting the amount of extension between the parts so as to inhibit the disengagement of the linking assembly through over-extension. Further the assembly allows for adjustment so that the relative positions of the two parts can be adjusted both with respect to the distance between them, (i.e., the relative longitudinal length) as well as with regard to the relative angle about the longitudinal axis of the two end clamping portions. Thus, the engagement is maintained but the clamping members can be adjusted in and out and rotated to suit the relative position of the rods. Further, the assembly can be disengaged in order to permit assembly with a second linking member having a variety of lengths in the extension.

The object of the invention is to provide a transverse connector which can provide for an adjustable length between two clamping members. The transverse connector has a two part telescoping linking portion including a vertical slot, or keyway, which allows the parts to be easily engaged prior to or during surgery but which limits the members from being inadvertently disassembled during implantation. Thus, in the event that a greater length needs to be spanned, linking part with a longer connector can be selected on the spot. Also, the relative angles of the clamp can be adjusted to account for deviations in the rods (such as might occur if the rods are bent as part of the procedure.)

DETAILED DESCRIPTION OF THE DRAWINGS

Figure 1:
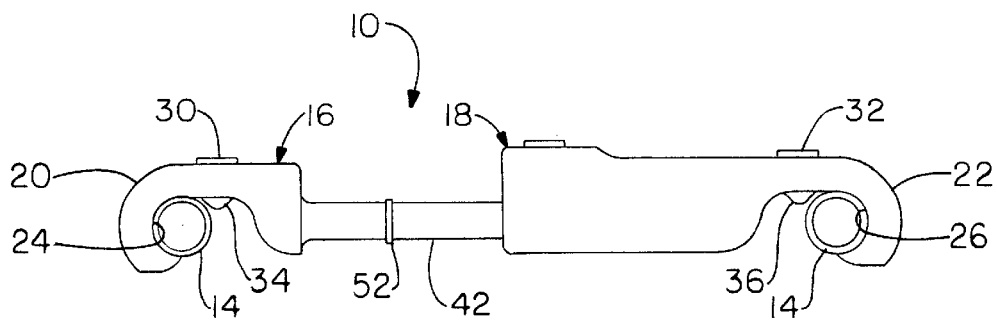
FIG. 1 is a side elevational view of the transverse connector of the present invention.
Figure 2A:
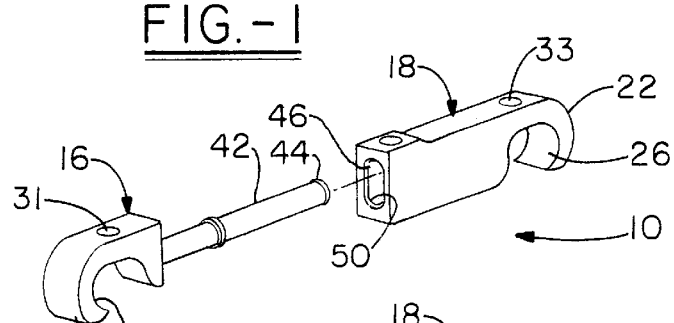
FIGS. 2A–2E are side perspective views of the transverse connector showing the assembly and contraction of the parts of the transverse connector.
Figure 2B:
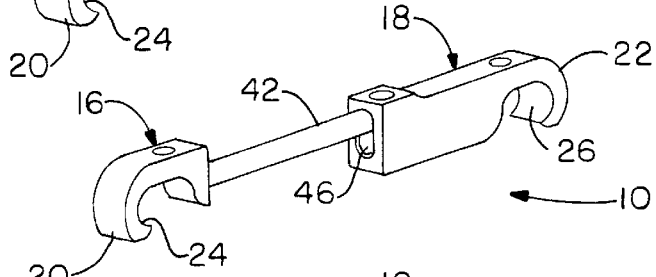
Figure 2C:
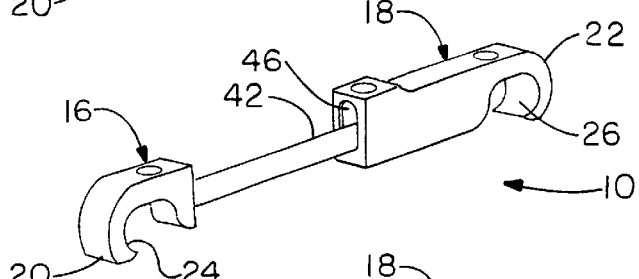
Figure 2D:
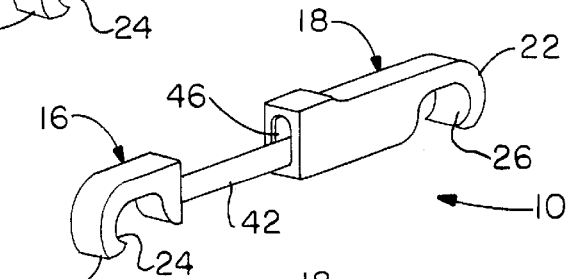
Figure 2E:
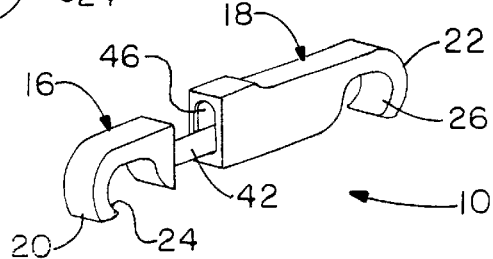
Figure 3A:
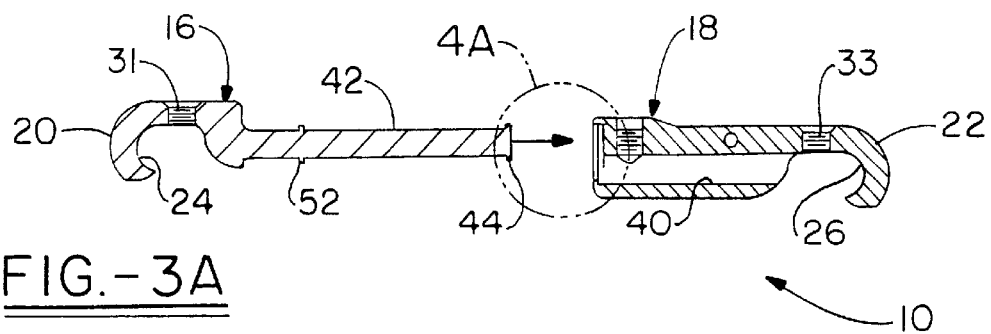
FIGS. 3A–3E are side cross-sectional views of the views shown in FIGS. 2A–2E.
Figure 3B:
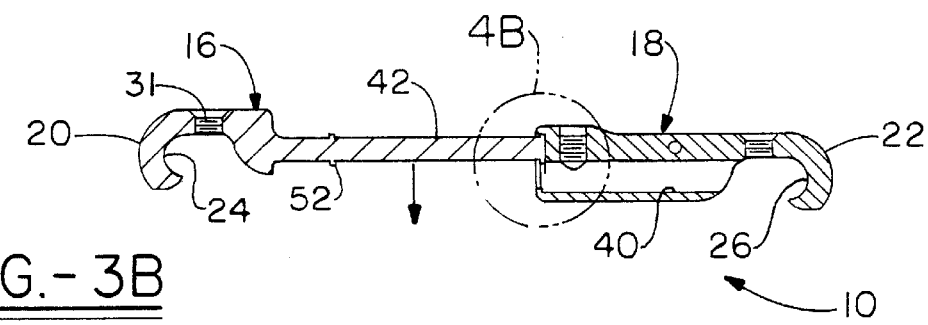
Figure 3C:
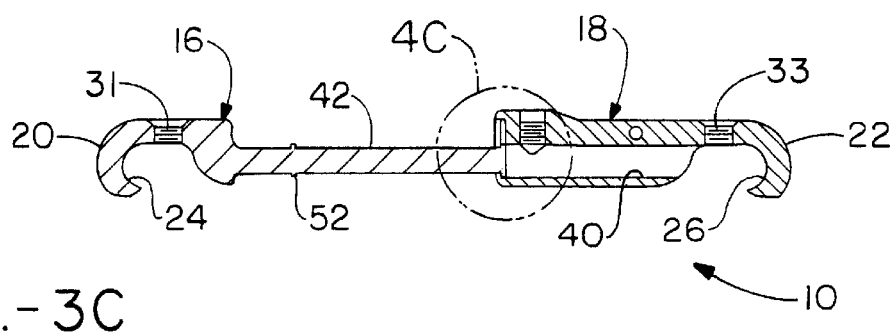
Figure 3D:
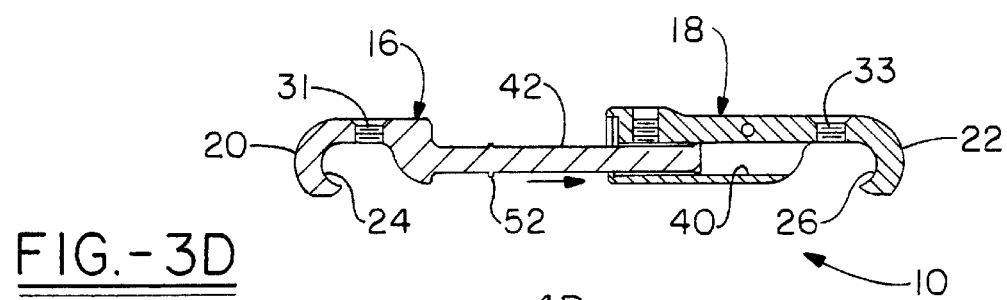
Figure 3E:
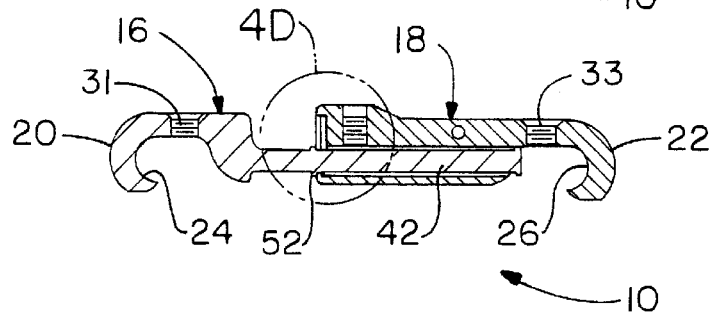

FIG. 1 illustrates a transverse connector 10 in accordance with the present invention. The connector 10 joins two elongated spinal stabilizers which are illustrated as rods 14, (but which could also comprise plates), which are fixed to a number of vertebrae by means of anchoring members which are not shown. The transverse connector has a linking assembly having a first 16 and a second part 18 which each have a end portion terminating in a clamp 20, 22. A variety of clamping structures could be used. They can be the same or different. For example, the clamp on one side could be closed while the clamp on the other side could be open. However, preferably, the clamps each include a recess 24, 26 which receive a respective rod. Setscrews 30, 32, which are received in threaded bores 31, 33, each terminate in a bevel area 34, 36 which biases the rod into a retaining contact with the recess. The longitudinal axis of the setscrew is offset from the longitudinal axis of the rod receiving recess so that the setscrew will bias the rod into the recess. The setscrews may include internal hexes, or other suitable torque driving means, for tightening. When they are assembled the recesses 20,26 are both open toward a central medial line or toward each other. This arrangement can be used for initial placement of the connector on the rods. Thus, the connector assembly can be placed onto the rods and then tightened with respect to the length.

The second member 18 of the transverse connector includes a bore 40, which receives a extension portion 42 which extends outwardly from the clamp 20 of the first part 16. The extension can move in and out of the bore to contract or expand the length of the space connected and the extension 42 can rotate in the bore 40 to change the relative angle of the openings of the rod recesses of the clamps to accommodate a varying relative angle of the longitudinal axis of the rods 14.

Figure 4A:
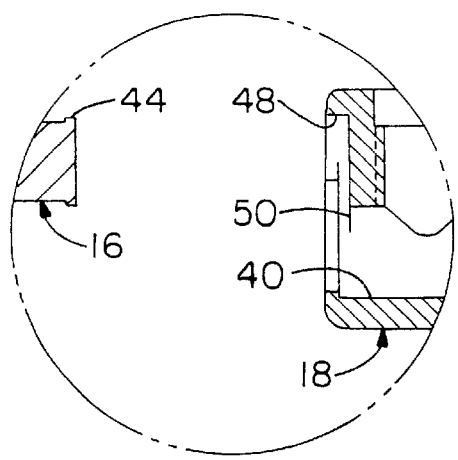
FIGS. 4A–4D are detailed drawings of the keyway shown in FIGS. 3A–3E.
Figure 4B:
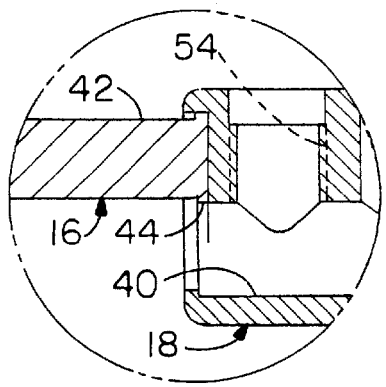
Figure 4C:
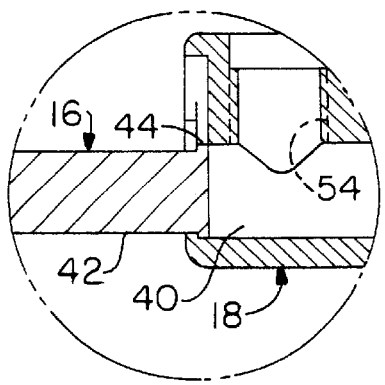
Figure 4D:
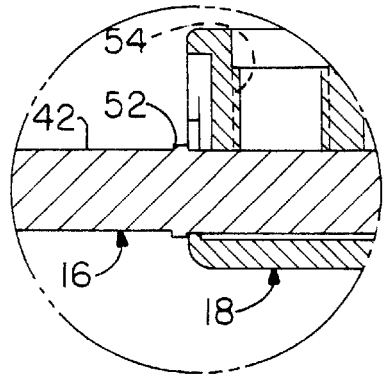

Further, the first and second members, 16, 18, include a limit mechanism which comprises a flanged end 44 on the extension 42. This flanged end 44 is inserted into a vertical keyway 46 which is a vertical slot in the first member having an enlarged opening 48 that is slightly larger than the diameter of the annular flange, and which will accommodate entry of the larger diameter flanged end 44. An undercut 50 is provided on either side of the keyway so as to allow for captured movement of the flanged end in the keyway, but allow for restriction against movement out of the keyway. A vertical slotted area is slightly wider than the diameter of the extension. Thus, the keyway restrains the flanged end in the vertical keyway 46 as it is slid downward toward the bore 40. When the extension comes to the end of the keyway 46, it can be moved inward in the bore 40. The first member can be telescoped into the second member until it encounters the second flanged area 52 as is shown in FIG. 4d. This limits the distance that the extension can travel into the bore, and inhibits lock-up. A setscrew is received in a bore 54 to lock the relative position of the first and second member.

What is claimed is:

1. A transverse connector which is able to join two stabilizer members of a spinal implant system, said transverse connector comprising an assembly having a first member having a first stabilizer clamp at one end and an extension, and a second member having a second stabilizer clamp at one end and a bore which receives the extension in a telescoping relationship along the direction of the longitudinal axis of the bore, and a keyway which receives the extension in a captured relationship and directs it into the bore opening and which acts so as to inhibit over extension of the assembly along the direction of the longitudinal axis of the bore wherein the keyway has an opeing which is offset from the longitudinal axis of the bore.

2. A transverse connector as set forth in claim 1 wherein the extension has a terminal annular flange and the vertical keyway has an enlarged opening joined with a slot defining an open passageway which has opposing undercut openings to define a with that can accommodate the terminal annular flange of the extension in a sliding relationship.

3. A transverse connector as set forth in claim 2 wherein the extension has an intermediate flange which has a diameter that is larger than the width of the slot.

4. A transverse connector as set forth in claim 2 wherein the keyway is a slot that is substantially transverse to the direction of the longitudinal axis of the bore and which terminates at the opening of the bore.

5. A transverse connector as set forth in claim 1 wherein the stabilizers are rods and at least one of said first and said second clamp comprise a recess which is laterally open to receive a rod and a biasing member which compresses the rod into a contact with the recess.

6. A transverse connector as set forth in claim 5 wherein both of said clamps comprise a recess which is laterally open to receive a rod and a biasing member which compresses the rod into a contact with the recess.

7. A transverse connector as set forth in claim 6 wherein said biasing member comprises a setscrew.

8. A transverse connector as set forth in claim 7 wherein said setscrew includes a bevel and has a longitudinal axis which is offset from the longitudinal axis of the recess, whereby the bevel biases the rod into contact with the recess.

9. A transverse connector which is able to join two rods members of a spinal implant system, said transverse connector comprising an assembly having a first member having a first rod clamp at one end and a cylindrical extension having a first outer diameter and an annular flanged area having a second outer diameter, and a second member having a second rod clamp at one end and cylindrical bore having an inner diameter and which receives the extension in a telescoping relationship along the direction of the longitudinal axis of the bore, and the inner diameter of the bore is larger than the second outer diameter of the extension and the bore is joined to a slot having an opening having a width which is greater than the second outer diameter of the extension, and having a restricted open passage having a width which is smaller than second outer diameter of the extension, but which is larger than the first outer diameter of the extension, and the open passage having an are a which includes opposing parallel undercut areas to define a keyway larger than the second diameter of the extension so as to permit a captured sliding of the second member in the keyway.

10. A transverse connector as set forth in claim 9 wherein the keyway slot substantially transverse to the direction of the longitudinal axis of the bore and which terminates at the opening of the bore.

11. A transverse connector as set forth in claim 10 wherein said first and said second clamp comprise a recess which is laterally open to receive a rod and a biasing member which compresses the rod into a contact with the recess.

12. A transverse connector as set forth in claim 11 wherein said biasing member comprises a setscrew.

13. A transverse connector as set forth in claim 12 wherein said setscrew includes a bevel and has a longitudinal axis which is offset from the longitudinal axis of the recess, whereby the bevel biases the rod into contact with the recess.

14. A transverse connector as set forth in claim 11 wherein the recess of the first clamp and the recess of the second clamp are open toward each other.

15. A transverse connector which is able to join two rods members of a spinal implant system, said transverse connector comprising an assembly having a first member having a first rod clamp at one end and a cylindrical extension having a first outer diameter and an annular flanged area having a second outer diameter, and a second member having a second rod clamp at one end, the first rod clamp and the second rod clamp each comprising a recess which is laterally open to receive a rod and a biasing member which compresses the rod into a contact with the recess, and said second member further having a cylindrical bore having an inner diameter and which receives the extension in a telescoping relationship along the direction of the longitudinal axis of the bore, and the inner diameter of the bore is larger than the second outer diameter of the extension and the bore is joined to a slot having an offset opening having a width which is greater than the second outer diameter of the extension, and having a restricted open passage having a width which is smaller than second outer diameter of the extension, but which is larger than the first outer diameter of the extension, and the open passage being joined by opposing parallel undercut areas to define a keyway larger than the second diameter of the extension so as to permit a captured sliding of the second member in the keyway.

16. A transverse connector as set forth in claim 15 wherein said biasing member comprises a setscrew.

17. A transverse connector as set forth in claim 16 wherein said setscrew includes a bevel and has a longitudinal axis which is offset from the longitudinal axis of the recess, whereby the bevel biases the rod into contact with the recess.

18. A transverse connector as set forth in claim 17 wherein the recess of the first clamp and the recess of the second clamp are open toward each other.

* * * * *

UNITED STATES PATENT AND TRADEMARK OFFICE
CERTIFICATE OF CORRECTION

PATENT NO.      : 6,616,668 B2
DATED           : September 9, 2003
INVENTOR(S)     : Moti Altarac et al.

It is certified that error appears in the above-identified patent and that said Letters Patent is hereby corrected as shown below:

<u>Title page,</u>
Item [75], Inventors, replace "Philip A. Meilinger" with -- Philip A. Mellinger --.

Signed and Sealed this

Twenty-third Day of December, 2003

JAMES E. ROGAN
*Director of the United States Patent and Trademark Office*